United States Patent
Nubel et al.

(10) Patent No.: US 8,492,583 B2
(45) Date of Patent: Jul. 23, 2013

(54) PROCESS FOR PURIFICATION OF AROMATIC CARBOXYLIC ACIDS

(75) Inventors: Philip O. Nubel, Naperville, IL (US); Muin S. Haddad, Naperville, IL (US); Jeffrey J. Foster, Sr., Bolingbrook, IL (US); Ricky L. Wittman, Aurora, IL (US)

(73) Assignee: BP Corporation North America Inc., Houston, TX (US)

( * ) Notice: Subject to any disclaimer, the term of this patent is extended or adjusted under 35 U.S.C. 154(b) by 273 days.

(21) Appl. No.: 11/721,462

(22) PCT Filed: Nov. 21, 2005

(86) PCT No.: PCT/US2005/042259
§ 371 (c)(1),
(2), (4) Date: Jun. 12, 2007

(87) PCT Pub. No.: WO2006/071407
PCT Pub. Date: Jul. 6, 2006

(65) Prior Publication Data
US 2008/0103333 A1  May 1, 2008

Related U.S. Application Data

(60) Provisional application No. 60/635,551, filed on Dec. 13, 2004.

(51) Int. Cl.
*C07C 51/42* (2006.01)
(52) U.S. Cl.
USPC .......................................... 562/487; 562/486
(58) Field of Classification Search
USPC ................................. 562/487, 486
See application file for complete search history.

(56) References Cited

U.S. PATENT DOCUMENTS

| | | | |
|---|---|---|---|
| 3,584,039 A | 8/1967 | Meyer | |
| 4,629,715 A | 12/1986 | Schroeder | |
| 4,892,972 A | 1/1990 | Schroeder | |
| 4,914,070 A | 4/1990 | Ledoux | |
| 4,933,492 A | 6/1990 | Schroeder | |
| 5,175,355 A | 12/1992 | Streich | |
| 5,217,930 A | 6/1993 | Dubots | |
| 5,354,898 A * | 10/1994 | Schroeder | 562/485 |
| 5,362,908 A | 11/1994 | Schroeder | |
| 5,427,761 A | 6/1995 | Grindatto | |
| 5,429,780 A | 7/1995 | Prin | |
| 5,449,654 A | 9/1995 | Prin | |
| 5,460,759 A | 10/1995 | Dubots | |
| 5,616,792 A | 4/1997 | Bartos | |
| 5,958,831 A | 9/1999 | Prin | |
| 6,184,178 B1 * | 2/2001 | Baluais et al. | 502/439 |
| 6,217,841 B1 | 4/2001 | Grindatto | |
| 6,251,819 B1 | 6/2001 | Prin | |

FOREIGN PATENT DOCUMENTS

| | | |
|---|---|---|
| GB | 1 259 297 | 1/1972 |
| WO | WO 98/30328 | 7/1998 |

OTHER PUBLICATIONS

A. Mori et al. "Pd/C Catalyzed Chemoselective Hydrogenation in the Presence of Diphenylsulfide" Organic Chemistry Portal, 2006, http://www.organic-chemistry.org/abstracts/lit1/331.shtm.

* cited by examiner

*Primary Examiner* — Sudhakar Katakam
(74) *Attorney, Agent, or Firm* — Stephen L. Hensley

(57) ABSTRACT

Impure aromatic carboxylic acids such as are obtained by liquid phase oxidation of feed materials comprising aromatic compounds with substituent groups oxidizable to carboxylic acid groups, or comprising aromatic carboxylic acid and one or more aromatic carbonyl impurities that form hydrogenated species more soluble in aqueous solvents or with less color or color-forming tendencies than the aromatic carbonyl impurity, are purified to an aromatic carboxylic acid product with lower levels of impurities by a process comprising contacting an aqueous solution comprising the impure aromatic carboxylic acid with hydrogen at elevated temperature and pressure with an attrition-resistance, acid stable catalyst composition comprising at least one hydrogenation catalyst metal and a support comprising relatively high surface area silicon carbide.

16 Claims, No Drawings

PROCESS FOR PURIFICATION OF AROMATIC CARBOXYLIC ACIDS

FIELD OF THE INVENTION

This invention relates to treating impure aromatic carboxylic acids to reduce levels of impurities and, more particularly, to purifying an impure terephthalic acid, such as a crude terephthalic acid product made by oxidation of a feed material comprising para-xylene, by catalytic hydrogenation of an aqueous solution of the product to be treated at elevated temperature and pressure in the presence of a catalyst comprising a metal having catalytic activity for hydrogenation and a support comprising silicon carbide.

BACKGROUND OF THE INVENTION

Purification of aromatic carboxylic acids by catalytic hydrogenation generally involves contacting an aqueous solution comprising an impure-acid product containing a desired aromatic carboxylic acid and impurities, such as a crude product made by oxidation of alkyl or other substituted aromatic feed materials, with hydrogen at elevated temperature and pressure in the presence of a catalyst comprising a metal with catalytic activity for hydrogenation disposed substantially on the surface of a solid carrier that is inert to the reactants and substantially insoluble in the liquid reaction mixture under reaction conditions. Hydrogenation of the aqueous solution of impure product permits separation of a purified, solid product from the hydrogenated reaction solution with a greater part, of impurities that affect quality of the desired aromatic carboxylic acid product contained in the remaining mother liquor as a result of hydrogenation either to species with greater aqueous solubility so that they remain dissolved in the mother liquor or to species less detrimental to quality if present in the purified product.

By way of example, terephthalic acid is widely used for the manufacture of polyethylene terephthalate polyesters used to make fibers, films and bottles, among other things, and is commonly made by heavy metal-catalyzed, liquid phase oxidation of para-xylene feed materials. The resulting crude oxidation product typically comprises the desired terephthalic acid and amounts of oxidation intermediates and other by-products, such as 4-carboxybenzaldehyde and p-toluic acid, and colored or color-forming species such as 2,6-dicarboxyfluorenone and 2,6-dicarboxyanthroquinone. Crude product with up to about 5,000 to 10,000 parts per million by weight ("ppmw") 4-carboxybenzaldehyde is not uncommon, and even amounts as low as 25 ppmw may be or correlate with impurity levels that may be detrimental to color of polyesters. As known from U.S. Pat. No. 3,584,039, purification of such crude and other impure terephthalic acid products by catalytic hydrogenation of an aqueous solution thereof at elevated temperatures and pressures converts 4-carboxylbenzaldehyde to hydroxymethyl benzoic acid, which in turn is converted to p-toluic acid, both of which are more soluble in the aqueous reaction liquid than terephthalic acid. Solid terephthalic acid with reduced levels of 4-carboxybenzaldehyde compared to the starting crude product can be crystallized from the reaction liquid while hydroxymethyl benzoic acid and p-toluic acid resulting from hydrogenation, of 4-carboxybenzaldehyde remain in solution. Hydrogenation of the crude product also converts colored and color-forming benzil, fluorenone and anthraquinone species such as 2,6-dicarboxyfluorenone and 2,6-dicarboxyanthroquinone, to corresponding colorless or less colored hydrogenated compounds. Related purification of impure isophthalic acid products, commonly made by liquid phase oxidation of meta-xylene feed materials, is disclosed in U.S. Pat. No. 4,933,492.

Conventional catalysts for practical commercial applications of such processes commonly comprise palladium carried on an inert, granular carbon support. Carbon supports are readily obtainable and chemically stable in the high temperature, acidic environments of purification reaction processes. However, carbon supports tend to be fragile and carbon-supported catalysts are easily damaged by process flow, pressure, and temperature upsets. Even minor damage can produce fine catalyst particles that can carry over with the product from a purification reactor and contaminate the purified product. In the case of purified terephthalic acid products, this contamination typically is manifested by high particulate contamination levels as indicated by standard measures such as $L^*$ values, which indicate grayness on a scale of 100 (corresponding to white or colorless) to 0 (corresponding to black), with values below 98 generally being considered poor for purified terephthalic acid.

More serious damage to carbon-supported catalysts can degrade a catalyst bed so extensively that reactor pressure drop becomes unacceptable. In such cases, the entire catalyst bed must be replaced. Another consequence of fragility of conventional carbon supports is loss of catalyst metals over the lifetime of a catalyst bed due to fines generated during upsets and catalyst loading and maintenance procedures. Spent catalyst beds containing 70% or even less of their initial catalyst metal contents are not uncommon. Loss of catalyst metals not only diminishes catalyst activity and lifetime but also creates a financial penalty from the lost metals themselves, especially in the case of expensive metals such as palladium.

A stronger catalyst support could reduce these difficulties with carbon supports. In that respect, properties such as crush strength and resistance to abrasion, formation of catalyst fines and loss of catalyst metals under conditions of handling, storage and use are important attributes of a support. Improvements in properties, however, are sometimes difficult to achieve without sacrifices in others. Beyond strength and abrasion resistance, utility of a support with particular catalyst metals for particular chemical reactions on a scale and under conditions suited to practical process applications is impacted, often unpredictably, by its activity, or lack of activity, for side reactions and affinity, or lack thereof, for adsorption and other surface phenomena under conditions of use, surface characteristics, such as surface area, pore size and volume, suited to facile and adequate catalyst metal loadings in catalyst preparation and effective reaction rates during catalyst use, and other factors. Titanium dioxide in rutile form, for example, is more strong and abrasion resistant than conventional carbon supports and, despite surface areas of only about 10 to about 40 $m^2/g$ as compared to hundreds to a thousand $m^2/g$ in the case of carbon supports, aromatic acid purification catalysts with catalyst metals supported on rutile titanium dioxide are known from U.S. Pat. No. 5,362,908. However, U.S. Pat. No. 5,616,792 indicates that color bodies remain after hydrogenation of crude terephthalic acid using the rutile titania-supported catalysts. Thus, despite improved strength and abrasion resistance compared to conventional carbon supports, performance of rutile titania-supported platinum and palladium catalysts in purification of terephthalic acid is inferior to that of catalysts with conventional carbon supports.

U.S. Pat. No. 3,584,039, noted above, describes catalyst metals and supports for purifying impure terephthalic acid by catalytic hydrogenation of impure terephthalic acid in aqueous liquid phase solution at elevated temperature and pressure, with preference given to Group VIII noble metals including ruthenium, rhodium, palladium, osmium, irridium and platinum as catalyst metals and suitable supports described as insoluble in water and unreactive with terephthalic acid at temperatures of at least 200° C., with carbons and charcoals being preferred. The patent reports that silicon carbide is not useable as a support due to high Si content (18,000 ppmw) of a residue remaining after contacting silicon carbide in an aqueous, 10 wt % terephthalic acid solution at 245° C. and elevated pressure for four hours. Commonly assigned U.S. Pat. No. 5,354,898 discloses purification of aromatic carboxylic acids using a carbon-supported hydrogenation catalyst metal such as palladium or rhodium in which purification reaction solution is passed through a bed or layer of non-catalytic particles with high abrasion resistance to reduce carryover of fine catalyst or carbon particles on removal of the solution from a purification reactor. Abrasion-resistant particles described in the patent have attrition loss according to ASTM D 4058-81 of less than 3%; silicon carbide is included in a list of examples.

Silicon carbide, as conventionally used as an abrasive and in refractory materials such as firebrick, rods and tubes, is commonly prepared commercially by fusing sand and coke in an electric furnace at temperatures above 2,200° C. The resulting silicon carbide forms extremely hard, dark, iridescent crystals that are free of porosity, insoluble in water and other common solvents and stable at high temperatures. It is not attacked by acids or alkalis or molten salts up to 800° C. In air, silicon carbide forms a protective silicon oxide coating at about 1200° C. Surface area of conventional silicon carbides typically is about 1 $m^2/g$. Extremely pure forms of silicon carbide are white or colorless and are used in semiconductors. More recently, U.S. Pat. No. 4,914,070 has reported silicon carbide in the form of porous agglomerates of submicroscopic grains made by heating a mixture of silicon dioxide and silicon at 1100-1400° C. under pressure of 0.1-1.5 hPa in a first reaction zone to generate silicon oxide vapors and contacting those vapors with reactive carbon in a divided state and having a surface area of at least 200 $m^2/g$ at 1100-1400° C. in a second reaction zone. The silicon carbides are further described as a carbonaceous substrate covered with silicon carbide crystallized in a face-centered cubic lattice, with specific surface areas of at least about 100 $m^2/g$ and color ranging from dark blue to mouse gray or to a dark shade of sea green. The compositions are said to have utility as supports for catalysts for petrochemical and high temperature reactions, such as rhodium or platinum catalysts for conversion of carbon monoxide and unburned hydrocarbons to $CO_2$ and nitrogen oxide to $NO_2$ in catalytic converters for internal combustion-engines, cobalt-molybdenum catalysts for petrochemical hydrotreatments such as hydrodesulphurization and hydrodemetallation, and for controlled oxidations to convert methane and other low molecular weight hydrocarbons to higher hydrocarbons. Related high surface area silicon and other metallic or metalloid refractory carbide compositions, said to be useful as supports for catalysts for chemical, petroleum and exhaust silencer reactions, and their manufacture, are also described in U.S. Pat. No. 5,217,930 and U.S. Pat. No. 5,460,759

U.S. Pat. No. 5,427,761 also describes production of silicon and other metal carbides, generally stated to be useful as catalysts or catalyst supports for chemical and petrochemical industries or for silencers, having BET surface areas of 10-200 $m^2/g$ and made by a process in which a reaction mixture of approximately stoichiometric proportions of a degassed carbon with surface area of at least 200 $m^2/g$ and a compound of a metal of which the carbide is to be formed and which is volatile under reaction conditions is introduced into a reactor scavenged with a flow of inert gas and heated at 900-1400° C. to volatilize the metal compound, reduce it with carbon and carburize the reduced product, and the result is cooled to a temperature such that the resulting metal carbide does not oxidize on contact with air, with control of inert gas flow to the reactor based on CO content of gas withdrawn therefrom.

Silicon carbide foams with specific surface areas of 10-50 $m^2/g$ and made in similar manner from a polyurethane foam as the starting carbon source are described in U.S. Pat. No. 5,429,780 and U.S. Pat. No. 5,449,654, as is impregnation of the silicon carbide with platinum, rhodium or palladium to form a catalyst, and use of the catalyst for oxidation of exhaust gases and in exhaust filters for diesel engines. Silicon carbide foams said to be useful as shaped catalyst supports as for exhaust pipes and such foams with ceria, rhodia and platinum deposited thereon are disclosed in U.S. Pat. No. 5,958,831. U.S. Pat. No. 6,217,841 describes silicon and metal carbides with large specific surface area (20-100 m2/g) and significant open macroporosity made similarly to the process of U.S. Pat. No. 5,427,761 but with a polyurethane or polyacrylonitrile carbon foam as the starting carbon. The metal carbides are said to have utility as catalyst supports for chemical and petrochemical industries although specific reactions and catalysts metals are not disclosed. U.S. Pat. No. 6,251,819 describes silicon carbide foams, preferably made from an organic foam as a starting carbon source, with surface areas of at least 5 $m^2/g$ and said to be useful in exhaust silencers. U.S. Pat. No. 6,184,178 reports catalyst supports in granular form essentially made up of silicon carbide beta crystallites having specific surface area of at least 5 $m^2/g$, and usually 10-50 $m^2/g$, and with crush resistance of 1-20 MPa according to ASTM D 4179-88a. The supports are said to be useful for chemical and petrochemical catalytic reactions such as hydrogenation, dehydrogenation, isomerization, decyclization, of hydrocarbides, although specific processes and catalyst metals are not described.

Use of high surface area silicon carbides as supports for catalysts for hydrogenation of impure aromatic carboxylic acids or for similar reactions at the elevated temperatures and pressures and in the extreme acidic environments of such hydrogenation processes is not reported, nor would utility in such processes have been expected from the instability of silicon carbide in terephthalic acid solution as reported in U.S. Pat. No. 3,584,039.

SUMMARY OF THE INVENTION

This invention provides a catalytic process for purification of an impure aromatic carboxylic acid product to an aromatic carboxylic acid product containing lower levels of impurities. The process uses a catalyst comprising a silicon carbide support having at least one hydrogenation catalyst metal supported on the surface thereof. The silicon carbide of the catalyst has greater surface area than conventional silicon carbide, such as that used as abrasives, but with improved abrasion and attrition resistance compared to conventional carbon supports for aromatic acid purification catalysts and improved stability in acidic solutions, even at high temperatures. These features also characterize the catalysts used according to the invented process. The improved properties of the catalysts and the supports from which they are prepared contribute to improvements in one or more of catalyst lifetime, process stability and reduced presence of catalyst particles in the purified product according to the invented process as compared to processes using conventional carbon-supported catalysts. The process provides product quality comparable to that obtained in hydrogenation processes using catalysts with conventional carbon supports.

In one embodiment, the impure aromatic carboxylic acid product that is purified according to the invented process comprises a crude aromatic carboxylic acid product obtained by liquid phase oxidation of a feed material comprising an aromatic compound with oxidizable substituents. The crude product of such oxidations comprises the aromatic carboxylic acid and one or more oxidation intermediates or by-products. Although the specific chemical compositions of intermediates and by-products will vary somewhat depending on factors such as the composition of the oxidation feed material and oxidation reaction conditions, and even for a given feed material are not fully known, they are known to comprise one or more aromatic carbonyl compounds, such as benzaldehydes, carboxybenzaldehydes, fluorenones and anthraquinones, that cause or correlate with undesirable color of the desired aromatic carboxylic acid product or of polyesters made therefrom and can be hydrogenated to species more soluble in aqueous solution than the aromatic carbonyl compounds and the aromatic carboxylic acid or to species with less color or color-forming tendencies. Hydrogenation according to the invention converts carbonyl substituents on aromatic nuclei of the impurities to corresponding hydrogenated groups, such as hydroxyalkyl and/or alkyl groups but without significant decarboxylation or ring hydrogenation reactions. Accordingly, in addition to impure aromatic carboxylic acid products comprising a crude aromatic carboxylic acid product obtained by liquid phase oxidation of a feed material comprising an aromatic compound with oxidizable substituents, the invention is useful for purification of impure aromatic carboxylic acid products comprising an aromatic carboxylic acid and such aromatic carbonyl impurities, whether present as intermediates or by-products from prior manufacturing steps or from any other source. Thus, in another aspect, the invention provides a process for purifying an impure aromatic carboxylic acid product comprising at least one aromatic carboxylic acid and at least one aromatic carbonyl impurity that forms a hydrogenated carbonyl-substituted aromatic product with greater solubility in aqueous solution or with less color or color-forming tendencies than the aromatic carbonyl impurity.

Briefly, the process according to the invention is a process for purifying an impure aromatic carboxylic acid comprising contacting with hydrogen under hydrogenation reaction conditions and in the presence of a catalyst an aqueous solution comprising impure aromatic carboxylic acid, wherein the catalyst comprises at least one hydrogenation, catalyst metal disposed substantially on the surface of a support comprising silicon carbide having a BET surface area of at least about 10 $m^2/g$, the catalyst has an initial attrition loss according to ASTM D-4058 less than about 1.2 wt % and the silicon carbide is substantially stable in the aqueous solution under the hydrogenation reaction conditions. Aromatic carboxylic acid product with reduced impurities is separated from the hydrogenated reaction solution, leaving impurities and their hydrogenated products substantially in solution in the resulting mother liquor.

Another embodiment of the invention provides a process for treating an impure aromatic carboxylic acid product that comprises a crude terephthalic acid obtained by a liquid phase oxidation of a feed material comprising para-xylene to a product that comprises terephthalic acid and at least one oxidation intermediate or by-product comprising forming an aqueous solution comprising the impure aromatic carboxylic acid product and contacting the aqueous solution with hydrogen at a temperature of about 200 to about 325° C. and pressure of about 500 to about 1500 psig in the presence of a catalyst comprising a hydrogenation catalyst metal disposed substantially on the surface of a support comprising silicon carbide having a BET surface area of at least about 10 $m^2/g$, wherein the catalyst has an initial attrition loss according to ASTM D-4058 of less than about 1.2 wt % and the silicon carbide is substantially stable in the aqueous solution at a temperature of about 200 to about 325° C. and pressure of about 500 to about 1500 psig.

In another embodiment the invention provides a process for treating an impure aromatic carboxylic acid product that comprises terephthalic acid and at least one of 4-carboxybenzaldehyde, hydroxymethyl benzoic acid, p-toluic acid, 2,6-dicarboxyfluorenone, 2,6-dicarboxyanthroquinone, 2,4',5-tricarboxybiphenyl, 2,5-dicarboxyphenyl-4-carboxyphenyl methane, 3,4'- and 4,4'-dicarboxybiphenyl, and 2,6-dicarboxyfluorene comprising forming an aqueous solution comprising the impure aromatic carboxylic acid product and contacting the aqueous solution with hydrogen at a temperature of about 200 to about 325° C. and pressure of about 500 to about 1500 psig in the presence of a catalyst comprising a hydrogenation catalyst metal-disposed substantially on the surface of a support comprising silicon carbide having a BET surface area of at least about 10 $m^2/g$, wherein the catalyst has an initial attrition loss according to ASTM D-4058 of less than about 1.2 wt % and the silicon carbide is substantially stable in the aqueous solution at a temperature of about 200 to about 325° C. and pressure of about 500 to about 1500 psig.

Surprisingly, we have also found that stability under reaction conditions of the catalysts used in the invented process is improved by conditioning the support used to make the invented catalysts in an aqueous or aqueous acidic liquid medium under conditions approaching or approximating those of the hydrogenation process. Accordingly, another aspect of the invention provides a process for improving stability of silicon carbide in acidic solution at elevated temperatures and pressures comprising contacting silicon carbide having a BET surface area of at least about 10 $m^2/g$ and attrition loss according to ASTM D-4058 of less than about 1.2 wt % in an aqueous liquid comprising up to 50 wt % organic carboxylic acid at a temperature of about 100 to about 325° C. and under pressure of about 1 to about 100 atmospheres for a time effective to improve acid stability of the silicon carbide. Surface area and attrition loss of the resulting silicon carbide are substantially retained as a result of such contacting.

DETAILED DESCRIPTION

Processes according to the invention provide desirable improvements in purity of impure aromatic carboxylic acids, typically with improved catalyst life and reduced reactor plugging and product contamination due to catalyst fines, than with carbon-supported catalysts. Aromatic carboxylic acid purification processes according to the invention may be conducted under more robust conditions conducive to higher throughputs or production rates than with granular carbon-supported catalysts as a consequence of the improved strength and attrition resistance of the silicon carbide supports of to the catalysts used according to the invention. Increased lifetime of the silicon carbide-supported catalysts allows longer operating periods between catalyst additions or replacements, and risk of reactor upsets due to plugging with catalyst fines and fugitive catalyst metal particles is reduced. The silicon carbide supports and catalysts based thereon also have good resistance to acidic environments, especially after conditioning in aqueous or aqueous acidic liquids according to an aspect of the invention. Significantly, a catalyst bed comprising solid particles of the silicon carbide-supported hydrogenation metal used according to the invention supported or suspended in an aqueous solution containing up to about 50 wt % aromatic carboxylic acid at temperatures up to about 325° C. and under pressures up to about 1500 psig, is substantially resistant to loss of catalyst fines and catalyst metal for prolonged periods of time, and with insignificant presence of silicon and silicon oxides in the purified product and reaction solution residues. The acid and high temperature resistance of the catalysts make them versatile for use not only in purification of aromatic carboxylic acids but also in other processes operated at high temperatures or involving acidic reactants, solvents, products or by-products. The increased strength and attrition resistance of the silicon carbide-supported hydrogenation catalysts as compared to carbon-supported catalysts, together with their ability to withstand acidic and high temperature conditions in use, afford greater opportunities for recovery of catalyst metals and re-use of supports than do conventional carbon supports.

Aromatic carboxylic acids of the impure products that are treated according to the invented process to reduce levels of impurities generally contain one or more aromatic nuclei and 1 to about 4 carboxylic acid groups. Examples include benzoic acid, phthalic acid, terephthalic acid, isophthalic acid, trimesic acid, trimellitic acid, and naphthalene dicarboxylic acids. Preferred aromatic carboxylic acids are dicarboxylic acids with a single aromatic ring and especially terephthalic acid. In commercial practice, these acids are often obtained by heavy metal-catalyzed, liquid phase oxidation of feed materials comprising aromatic compounds with oxidizable substituents, such as toluene, xylenes, trimethylbenzenes and dimethyl and diethyl naphthalenes.

The impure aromatic carboxylic acid to be purified according to the invention also comprises one or more impurities. In the case of an impure aromatic carboxylic acid comprising a crude product obtained by liquid phase oxidation of feed materials comprising aromatic compounds with oxidizable substituent groups, impurities comprise oxidation by-products or intermediates. In the case of a crude terephthalic acid product obtained by liquid phase oxidation of feed materials such as p-xylene, common oxidation intermediates and by-products are one or more of 4-carboxybenzaldehyde, hydroxymethyl benzoic acid, p-toluic acid, 2,6-dicarboxyfluorenone, 2,6-dicarboxyanthroquinone, 2,4',5-tricarboxybiphenyl, 2,5-dicarboxyphenyl-4-carboxyphenyl methane, 3,4'- and 4,4'-dicarboxybiphenyl, and 2,6-dicarboxyfluorene. Among known impurities, at least 4-carboxybenzaldehyde, 2,6-dicarboxyfluorenone and 2,6-dicarboxyanthroquinone are known to cause or correlate with color of terephthalic acid or its polyesters.

More generally, and without regard to source or method of manufacture of the impure aromatic carboxylic acid to be purified, impurities that can be hydrogenated according to the invention to purify impure aromatic carboxylic acids in which they are present commonly comprise one or more aromatic carbonyl compounds, such as aromatic aldehydes and ketones with one or more aromatic rings. Specific examples include benzaldehyde, 2-, 3- and 4-carboxybenzaldehydes, 2,6-dicarboxyfluorenone, 2,4',5-tricarboxybiphenyl, 2,5-dicarboxyphenyl-4-carboxyphenyl methane, 3,4'- and 4,4'-dicarboxybiphenyl and 2,6-dicarboxyanthroquinone. Hydrogenation of such compounds results in conversion of carbonyl groups to corresponding hydroxyalkyl and alkyl groups. The resulting hydrogenated species are typically more soluble in aqueous solvents than the original carbonyl species and than the desired aromatic acid product, or are less colored or less prone to imparting color to polyesters or other products made from the desired product, thereby facilitating separation of the more soluble hydrogenated carbonyl compounds from the desired product by crystallization and leaving a greater portion of colored or color-forming species in the reaction liquid or mother liquor from which the desired product is crystallized. Hydrogenation according to the invention is selective to the carbonyl species, and proceeds without substantial ring hydrogenation of either the aromatic carbonyls or of the desired aromatic acids, and also without substantial decarbonylation or decarboxylation of carboxylic acid substituents on the aromatic rings.

Amounts of impurities, such as oxidation by-products and intermediates and/or aromatic carbonyl compounds, present in the impure aromatic carboxylic acids to be treated according to the invention vary with the nature and source of the impurities. Generally, any amount of such impurities may be present without hindering effectiveness of the invention, although if present at high enough levels, other separation techniques may be more practical or economically efficient. Aromatic carboxylic acids as obtained in liquid phase oxidations of alkyl aromatic feed materials often contain as much as 1 to 2 wt % impurities, with up to about 1 wt % being more common in commercial practice.

Hydrogenation of impure aromatic carboxylic acids to reduce impurities levels according to the invention is conducted with the impure acid in aqueous solution. Water is a preferred solvent for the process although lower monocarboxylic acids, alone or mixed with water, may also be used. When using water as the purification solvent, minor amounts of acetic acid, which is a common solvent used in manufacture of crude aromatic carboxylic acids, may be present as a result of incomplete removal thereof from the product to be purified or other sources. Concentrations of impure aromatic carboxylic acid to be treated in the purification solvent generally are low enough that the impure acid is substantially dissolved and high enough for practical process operations and efficient use and handling of solvents. Suitably, solutions comprising about 5 to about 50 parts by weight impure aromatic carboxylic acid per hundred parts by weight solution at process temperatures provide adequate solubility for practical operations. Preferred feed solutions contain about 10 to about 40 wt % and more preferably about 20 to about 35 wt % impure aromatic carboxylic acid at the temperatures used for treatment.

Purification of the aqueous solution is conducted at elevated temperatures and pressures. Temperatures range from about 200 to about 370° C., with about 225 to about 325° C. being preferred and about 240 to about 300° C. being most preferred. Purification is conducted at a pressure sufficient to maintain a liquid phase comprising the aqueous reaction solution. Total pressure is at least equal to, and preferably exceeds, the sum of the partial pressures of the hydrogen gas introduced to the process and water vapor that boils off from the aqueous reaction solution at the temperature of operation. Preferred pressures are about 500, and more preferably about 1000, to about 1500 psig.

The aqueous solution of impure aromatic carboxylic acid is contacted with hydrogen under hydrogenation conditions as described above in a suitable reaction vessel capable of withstanding the temperature and pressures under which hydrogenation is conducted and also the acidic nature of the liquid reaction mixture. A preferred reactor configuration is a cylindrical reactor with a substantially central axis positioned with the axis vertically disposed when the reactor is in use. Both upflow and downflow reactors can be used. Catalyst typically is present in the reactor in one or more fixed beds of particles maintained with a mechanical support for holding the catalyst particles in the bed while allowing relatively free passage of reaction solution therethrough. A single catalyst bed is often preferred although multiple beds of the same or different catalyst or a single bed layered with different catalysts, for example, with respect to particle size, hydrogenation catalyst metals or metal loadings, or with catalyst and other materials such as abrasives to protect the catalyst, also can be used and may provide benefits. Mechanical supports in the form of flat mesh screens or a grid formed from appropriately spaced parallel wires are commonly employed. Other suitable catalyst retaining means include, for example, a tubular Johnson screen or a perforated plate. The mechanical support for the catalyst bed is constructed of a material that is suitably resistant to corrosion, due to contact with the acidic reaction solution, and strong enough to efficiently retain the catalyst bed. Most suitably, supports for catalyst beds have openings of about 1 mm or less and are constructed of metals such as stainless steel, titanium or Hastelloy C.

In a preferred embodiment of the invention, aqueous solution of impure aromatic carboxylic acid to be purified is added to the reactor vessel at elevated temperature and pressure at a position at or near the top portion of the reactor vessel, and the solution flows downwardly through the catalyst bed contained in the reactor vessel in the presence of hydrogen gas, wherein impurities are reduced with hydrogen, in many cases forming hydrogenated products with greater solubility in the reaction mixture than the desired aromatic carboxylic acid or with less color or color-forming tendencies. In such a preferred mode, the impure carboxylic acid is purified and the purified product is removed from the reactor vessel at a position at or near a lower portion or the bottom of the reactor.

The reactor may be operated in several modes. In one operating mode, a predetermined liquid level may be maintained in the reactor and, for a given reactor pressure, hydrogen can be fed at a rate sufficient to maintain the predetermined liquid level. The difference between the actual reactor pressure and the vapor pressure of the vaporized purification solution present in the reactor head space is the hydrogen partial pressure in the head space. Alternatively, hydrogen can be fed mixed with an inert gas such as nitrogen or water vapor, in which case the difference between the actual reactor pressure and the vapor pressure of the vaporized reaction solution present is the combined partial pressure of hydrogen and the inert gas admixed therewith. In this case the hydrogen partial pressure may be calculated from the known relative amounts of hydrogen and inert gas present in the admixture.

In another operating mode, the reactor can be filled with the aqueous liquid reaction mixture so that there is no reactor vapor space. In such an embodiment, the reactor is operated as a hydraulically full system with dissolved hydrogen being fed to the reactor by flow control. In such an embodiment, the concentration of hydrogen in solution may be modulated by adjusting the hydrogen flow rate to the reactor. If desired, a pseudo-hydrogen partial pressure value may be calculated from the solution hydrogen concentration which, in turn, may be correlated with the hydrogen flow rate to the reactor.

When operating such that process control is effected by adjusting the hydrogen partial pressure, the hydrogen partial pressure in the reactor is preferably in the range of 10 pounds per square inch gauge to 200 pounds per square inch gauge (69-1379 kPa) or higher, depending on pressure rating of the reactor, impurities levels of the impure aromatic carboxylic acid, activity and age of the catalyst and other considerations known to persons skilled in the art. In the operating mode in which process control is effected by directly adjusting the hydrogen concentration in the feed solution, the latter usually is less than saturated with respect to hydrogen and the reactor itself is hydraulically full. Thus, an adjustment of the hydrogen flow rate to the reactor will result in the desired control of hydrogen concentration in the solution.

The space velocity, reported as weight of the impure aromatic acid per weight of catalyst per hour, during hydrogenation is typically about 1 hour$^{-1}$ to about 25 hour$^{-2}$, and preferably about 2 hours$^{-1}$ to about 15 hours$^{-1}$. The residence time of the purification liquid stream in the catalyst bed varies depending on the space velocity.

After hydrogenation, the hydrogenated stream comprising aromatic carboxylic acid and hydrogenated aromatic impurities having greater solubility in the aqueous reaction liquid than their unhydrogenated precursors is cooled to separate a purified, solid aromatic carboxylic acid from the hydrogenated reaction liquid, leaving a liquid product, frequently referred to as a purification mother liquor, in which hydrogenated impurities remain dissolved. Separation is commonly achieved by cooling to a crystallization temperature, which is sufficiently low for crystallization of the purified aromatic acid to occur, thereby producing crystals within the liquid phase. The crystallization temperature is sufficiently high so that impurities and their reduction products resulting from hydrogenation remain dissolved in the liquid phase. Crystallization temperatures generally range up to 160° C. and preferably up to about 150° C. In continuous operations, separation normally comprises removing the hydrogenated reaction solution from the purification reactor and crystallization of aromatic carboxylic acid in one or more crystallization vessels. When conducted in a series of stages or separate crystallization vessels, temperatures in the different stages or vessels can be the same or different and preferably decrease from each stage or vessel to the next. Thereafter, crystallized, purified aromatic carboxylic acid product is recovered from the mother liquor, including hydrogenated impurities dissolved therein. Recovery of the crystallized purified product is commonly conducted by centrifuging or by filtration. Physical integrity and chemical stability of the catalysts used according to the invention are such that silicon/silica content of the purified aromatic carboxylic acid products obtained from the invented process typically is less than about 15 ppmw, and preferably less than about 10 ppmw. Silicon content of purification mother liquor remaining, after separation of purified aromatic carboxylic acid product from the hydrogenated reaction solution is less than about 500 ppmw and preferably less than about 100 ppmw.

Purification reactor and catalyst bed configurations and operating details and crystallization and product recovery techniques and equipment useful in the process according to this invention are described in further detail in U.S. Pat. No. 4,629,715, U.S. Pat. No. 4,892,972, U.S. Pat. No. 5,175,355, U.S. Pat. No. 5,354,898, U.S. Pat. No. 5,362,908 and U.S. Pat. No. 5,616,792 which are incorporated herein by reference.

The catalyst used in invented process comprises a relatively high surface area support comprising silicon carbide and one or more metals having catalytic activity for hydrogenation of impurities in impure aromatic carboxylic acid products, such as oxidation intermediates and by-products and/or aromatic carbonyl species. Suitable catalyst metals are the Group VIII metals of the Periodic Table of Elements (IUPAC version), including palladium, platinum rhodium, osmium, ruthenium, iridium, and combinations thereof. Palladium or combinations of such metals that include palladium are most preferred. Suitable metal loadings generally are about 0.1 wt % to about 5 wt % based on total weight of the support and catalyst metal or metals. Preferred catalysts for conversion of impurities present in impure aromatic carboxylic acid products comprising crude terephthalic acid obtained by liquid phase oxidation of a feed material comprising paraxylene contain about 0.1 to about 3 wt % and more preferably about 0.2 to about 1 wt % hydrogenation metal. For such uses, the metal most preferably comprises palladium.

For practical applications, the catalyst is most preferably used in particulate form, for example as pellets, extrudate, spheres or granules, although other solid forms also are suitable. Particle size of the catalyst is selected such that a bed of catalyst particles is easily maintained in a suitable reactor for the purification process but permits flow of the purification reaction mixture through the bed without undesirable pressure drop. Preferred average particle sizes are such that catalyst particles pass through a 2-mesh screen but are retained on a 24-mesh screen (U.S. Sieve Series) and more preferably pass through a 4-mesh screen but are retained on a 12-mesh and, most preferably, 8-mesh screen.

The catalyst used in the invented process has BET surface areas of at least about 10 $m^2$/gram. While low by comparison to surface areas of conventional carbon-supported catalysts, surface areas are generally an order of magnitude greater than those of conventional silicon carbides used as abrasives and are satisfactory for use according to the invented process. Preferably, surface areas of the catalysts are at least about 15, and more preferably at least about 20 $m^2$/gram. Catalyst surface area is substantially attributable to surface area of the support and, while known high surface area silicon carbides are generally believed to have surface areas in the range of 10 to about 200 $m^2$/gram, still higher surface area silicon carbides and catalysts comprising such supports and one or more hydrogenation catalyst metals as described herein are contemplated according to the invention provided they are resistant to attrition and stable in aqueous acid solutions at elevated temperatures as described herein.

Attrition resistance of the catalysts used in the invented process is determined according to ASTM D-4058, with attrition loss of the catalysts before use in the invented process, also referred to herein as initial attrition loss, being less than about 1.2 wt % and preferably less than about 1 wt %. Attrition resistance of the catalysts is attributable to that of the silicon carbide support included in the catalyst. The attrition resistance of the relatively high surface silicon carbides used as supports according to the invention is significantly greater than that of conventional carbons used as supports for catalysts for purification of aromatic carboxylic acids.

The catalysts used in the invented process exhibit surprising stability in aqueous acidic solutions, even at the elevated temperatures and pressures used in the invented process. In general, the catalysts lose less than about 2% of their weight, and preferably no more than about 1 wt %, after 20 days exposure to 20 wt % solution of terephthalic acid at about 275° C. and 850 psig.

The silicon carbide support used to prepare the catalysts used in the invented process generally have BET surface areas and attrition resistance according to ASTM D-4058 as described above with regard to the catalysts themselves. The acid stability of the supports is greater than that of the silicon carbides described in U.S. Pat. No. 3,584,039. Supports can be obtained by any suitable technique for making relatively high surface area, attrition resistant silicon carbides, such as by high temperature reaction of a silicon compound that volatilizes at the reaction temperature with a high surface area carbon. Examples of methods for preparing high surface area, attrition-resistant silicon carbides are found in U.S. Pat. No. 4,914,070, U.S. Pat. No. 5,427,761 and other patents cited herein. In one embodiment of the invention, silicon carbide comprising beta crystallites, and preferably with a substantial absence of alpha crystallites, is a preferred form of silicon carbide. U.S. Pat. No. 6,184,178, incorporated herein by reference, discloses preparation of a silicon carbide in beta crystallite form.

A specific example of the high surface area silicon carbide support useful for making the catalysts used according to the invented process is a silicon carbide that is commercially available from SICAT Corporation as CTS-10 in the form of 3 mm diameter extrudate and having a BET surface area of 21 $m^2$/gram, attrition loss according to ASTM D4058 of about ½ to about 1 wt.

The catalyst used in the invented process can be made by any suitable method for depositing catalyst metal substantially on the surface of a support. Typically, support particles, such as pellets, granules, extrudate, are contacted with a solution of catalyst metal or a compound thereof in water or another solvent that is inert to the support and easily removed, after which the solvent is removed, such as by drying at ambient or elevated temperature. Incipient wetness techniques, in which a support is contacted with a solution of the catalyst metal compound in an amount that just wets the support and then the resulting wetted support is dried, are known and well suited to manufacture of the catalysts. Other techniques, such as spraying a solution of catalyst metal compound onto the silicon carbide support also are suitable. Suitable catalyst metal compounds are well known and include nitrates and chlorides, specific examples being palladium chloride and palladium nitrate, both of which are water-soluble. Post-treatments, such as high temperature calcinations in the presence of air or nitrogen, and reduction with hydrogen also can be used if desired and may yield catalysts with additional advantages or characteristics of interest. Pretreatment of the silicon carbide particles used for catalyst preparation by contacting the same with water or an aqueous acid solution at temperatures and pressures sufficient to boil the aqueous liquid while maintaining a liquid phase is beneficial for improving aqueous acid stability of the silicon carbide and catalysts prepared therefrom under hydrogenation conditions used according to the invented process. Preferably, the silicon carbide particles are treated with an aqueous solution comprising up to about 50 wt % organic carboxylic acid at temperatures in the range of about 100 to about 325° C. and pressures of about 1 to about 100 atmospheres. Practically, treating times of about 1 to about 24 hours are suitable.

In a more specific embodiment of the invention, the impure aromatic carboxylic acid product to be purified according to the invention comprises a crude aromatic carboxylic acid product obtained by liquid phase oxidation of a feed material comprising at least one aromatic compound with substituents oxidizable to a carboxylic acid groups. Such oxidations are commonly conducted in a liquid phase reaction mixture comprising a monocarboxylic acid solvent and water with oxygen in the presence of a heavy metal catalyst.

Feed materials for manufacture of such crude aromatic acid products generally comprise an aromatic hydrocarbon substituted with at least one group that is oxidizable to a carboxylic acid group. The oxidizable substituent or substituents can be an alkyl group, such as a methyl, ethyl or isopropyl group. The substituents also can include one or more groups already containing oxygen, such as a hydroxyalkyl, formyl or keto group. The substituents can be the same or different. The aromatic portion of feedstock compounds can be a benzene nucleus or it can be bi- or polycyclic, such as a naphthalene nucleus. The number of oxidizable substituents on the aromatic portion of the feedstock compound can be equal to the number of sites available on the aromatic portion, but is generally fewer than all such sites, preferably 1 to about 4 and more preferably 1 to 3. Examples of useful feed compounds include toluene, ethylbenzene, o-xylene, p-xylene, m-xylene, 1-formyl-4-methylbenzene, 1-hydroxymethyl-4-methylbenzene, 1,2,4-trimethyl-benzene, 1-formyl-2,4-dimethylbenzene, 1,2,4,5-tetramethylbenzene, and alkyl-, acyl-, formyl- and hydroxymethyl-substituted naphthalene compounds, such as 2,6- and 2,7-dimethylnaphthalenes, 2-acyl-6-methylnaphthalene, 2,6-diethylnaphthalene, 2-formyl-6-methylnaphthalene and 2-methyl-6-ethylnaphthalene.

For manufacture of a crude aromatic acid product by oxidation of corresponding aromatic feed pre-cursors, e.g., manufacture of isophthalic acid from meta-disubstituted benzenes, terephthalic acid from para-disubstituted benzenes, trimellitic acid from 1,2,4-trisubstituted benzenes, naphthalene dicarboxylic acids from disubstituted naphthalenes, it is preferred to use relatively pure feed materials, and more preferably, feed materials in which content of the pre-cursor corresponding to the desired acid is at least about 95 wt. %, and more preferably at least 98% or even higher. A preferred aromatic feed for use to manufacture terephthalic acid comprises para-xylene. A preferred feed for isophthalic acid comprises meta-xylene. A preferred feed for trimellitic acid comprises 1,2,4-trimethylbenzene.

Oxidant gas used for the liquid phase oxidations comprises molecular oxygen. Air is conveniently used as a source of molecular oxygen. Oxygen-enriched air, pure oxygen and other gaseous mixtures comprising at least about 10% molecular oxygen also are useful.

Catalysts used in such liquid phase oxidations comprise materials that are effective to catalyze oxidation of the aromatic hydrocarbon feed to aromatic carboxylic acid. Preferably, the catalyst is soluble in the liquid oxidation reaction body to promote contact among catalyst, oxygen and liquid feed; however, heterogeneous catalyst or catalyst components may also be used. Typically, the catalyst comprises at least one heavy metal component such as a metal with atomic weight in the range of about 23 to about 178. Examples include cobalt, manganese, vanadium, molybdenum, chromium, iron, nickel, zirconium, cerium or a lanthanide metal such as hafnium. Preferably, catalyst comprising one or both of cobalt and manganese is used. Soluble forms of these metals include bromides, alkanoates and bromoalkanoates; specific examples include cobalt acetate and bromide, zirconium acetate and manganese acetate and bromide.

The catalyst preferably is used in combination with a promoter. The promoter is used to promote oxidation activity of the catalyst metal, preferably without generation of undesirable types or levels of by-products, and is preferably used in a form that is soluble in the liquid reaction mixture. Preferably the promoter comprises bromine, including elemental, ionic or organic forms thereof. Examples include Br, HBr, NaBr, KBr, $NH_4Br$, bromobenzenes, benzyl-bromide, bromo acetic acid, dibromo acetic acid, tetrabromoethane, ethylene dibromide and bromoacetyl bromide. Other promoters include aldehydes and ketones, such as acetaldehyde and methyl ethyl ketone.

A solvent for the feed material, soluble catalyst materials and promoter is desirably used in the process. Solvents comprising an aqueous carboxylic acid, and especially a lower alkyl (e.g., $C_{1-6}$) monocarboxylic acid, are preferred because they tend to be only sparingly prone to oxidation under typical oxidation reaction conditions used for manufacture of aromatic acids, and can enhance catalytic effects in the oxidation. Specific examples of suitable carboxylic acids include acetic acid, propionic acid, butyric acid, benzoic acid and mixtures thereof. Ethanol and other co-solvent materials which oxidize to monocarboxylic acids under the aromatic acid oxidation reaction conditions also can be used as is or in combination with carboxylic acids with good results.

Proportions of the feed, catalyst, oxygen and solvent are not critical and vary not only with choice of feed materials and intended product but also choice of process equipment and operating factors. Solvent to feed weight ratios suitably range from about 1:1 to about 10:1. Oxygen typically is used in at least a stoichiometric amount based on feed but not so great that unreacted oxygen escaping from the liquid body to the overhead gas phase forms a flammable mixture with other components of the gas phase. Catalysts suitably are used in weights providing about 100 to about 3000 ppm catalyst metal based on feed weight. Promoter concentrations also generally range from about 100 to about 3000 ppm based on weight of the liquid feed, with about 0.1 to about 2 milligram-atoms of promoter suitably used per milligram-atom of catalyst metal.

Oxidation of aromatic feed materials to crude product comprising aromatic acid is conducted under oxidation reaction conditions. Temperatures in the range of about 120 to about 250° C. are generally suitable, with about 150 to about 230° C. preferred. Pressure in the reaction vessel is at least high enough to maintain a substantial liquid phase comprising feed and solvent in the vessel. Generally, pressures of about 5 to about 35 $kg/cm^2$ gauge are suitable, with preferred pressures for particular processes varying with feed and solvent compositions, temperatures and other factors. Solvent residence times in the reaction vessel can be varied as appropriate for given throughputs and conditions, with about 20 to about 150 minutes being generally suited to a range of processes. For processes in which the aromatic acid product is substantially soluble in the reaction solvent, such as in the manufacture of trimellitic acid by oxidation of psuedocumene in acetic acid solvent, solid concentrations in the liquid body are negligible. In other processes, such as oxidation of xylenes to isophthalic or terephthalic acids, solids contents can be as high as about 50 wt. % of the liquid reaction body, with levels of about 10 to about 35 being more typical. As will be appreciated by those skilled in the manufacture of aromatic acids, preferred conditions and operating parameters vary with different products and processes and can vary within or even beyond the ranges specified above.

Crude aromatic carboxylic acid products of such liquid phase oxidation processes include impurities comprising oxidation intermediates and by-products, typically including one or more aromatic carbonyl species that cause or correlate with color in the desired aromatic acid product or in polyesters made therefrom. Examples of those intermediates and by-products include aldehydes and ketones such as the carboxybenzaldehydes, fluorenones and dicarboxyanthroquinones described above. Impurities levels up to 2 wt % or even higher, depending on feed materials, operating parameters and process efficiency, are not uncommon and can be enough to affect product quality of the desired carboxylic acid product or downstream products thereof.

In a particular embodiment, the invention is used for the manufacture of a purified aromatic carboxylic acid comprising terephthalic acid from a crude aromatic carboxylic acid product comprising terephthalic acid and impurities obtained by boiling liquid phase oxidation of an aromatic hydrocarbon feed comprising para-xylene. Acetic acid or aqueous acetic acid is a preferred solvent, with a solvent to feed ratio of abut 2:1 to about 5:1 being preferred. The catalyst preferably comprises cobalt, manganese or a combination thereof, and a source of bromine soluble in the solvent is preferably used as promoter. Cobalt and manganese preferably are used in amounts providing about 100 to about 800 ppmw based on feed weight. Bromine preferably is present in an amount such that the atom ratio of bromine to catalyst metal is about 0.1:1 to about 1.5:1.

Oxygen-containing gas is provided to the liquid phase reaction mixture at a rate effective to provide at least about 3 moles molecular oxygen per mole of aromatic feed material and, in conjunction with removal of reactor off-gases, such that unreacted oxygen in the vapor space above the liquid reaction body is below the flammable limit. When air is the source of oxygen, the limit is about 8 mole % when measured after removal of condensable compounds.

Oxidation preferably is conducted at temperatures of about 160 to about 225° C. under pressure of about 5 to about 20 kg/cm² gauge. Under such conditions, contact of the oxygen and feed material in the liquid body results in formation of solid terephthalic acid crystals, typically in finely divided form. Solids content of the boiling liquid slurry typically ranges up to about 40 wt. % and preferably from about 20 to about 35 wt. %, and water content typically is about 5 to about 20 wt. % based on solvent weight. Boiling of the liquid body for control of the reaction exotherm causes volatilizable components of the liquid body, including solvent and water of reaction, to vaporize within the liquid. Unreacted oxygen and vaporized liquid components escape from the liquid into the reactor space above the liquid. Other species, for example nitrogen and other inert gases that are present if air is used as an oxygen source, carbon oxides, and vaporized by-products, e.g., methyl acetate and methyl bromide, also may be present in the overhead vapor.

Crude product from the oxidation is separated from the liquid reaction mixture, typically by crystallization at reduced temperature and pressure, and the resulting solid is recovered by filtration or centrifuging. The recovered crude terepthalic acid comprises 4-carboxybenzaldehyde, typically in amounts ranging from about 500 to about 5000 ppmw, and frequently up to several hundred ppmw of color formers such as 2,6-dicarboxyfluorenone and 2,6-dicarboxyanthroquinone. Purification of the crude product according to the invention typically reduces levels of 4-carboxybenzaldehyde in the purified terephthalic acid to below about 100 ppmw, preferably about 25 ppmw or less, and color former concentrations to negligible amounts.

The invention is further described in the following examples, which are presented for purposes of illustration, not limitation.

EXAMPLE 1

A catalyst with palladium supported on silicon carbide (Pd/SiC) was prepared using a silicon carbide in the form of 3 mm diameter extrudate and having a BET surface area of 21 m²/g. The silicon carbide, identified as CTS-10 from SICAT Corporation, had metallic impurities content of less than about ½ wt % and was substantially free of silica and of alpha silicon carbide crystallites.

The catalyst was prepared by an incipient wetness method in which 1.36 grams of palladium nitrate hydrate (38.61 wt % Pd) were first dissolved in 16 ml deionized water to which a few drops of concentrated nitric acid had been added. The resulting cloudy solution was then added to 50 g of the silicon carbide in a glass bottle and the bottle was shaken gently for several minutes to thoroughly mix the solution and solids. The solids were then allowed to dry at room temperature under a flow of nitrogen gas until the liquid had evaporated. The dried solids were charged to a titanium autoclave reactor to which hydrogen was charged under pressure of 200 psi and the autoclave was heated gradually over about ½ hour to about 121° C. and then allowed to cool, after which the catalyst was removed and dried in a vacuum oven at about 66° C. overnight. Inductively Coupled Plasma analysis of the resulting solid showed that it contained 0.89 wt % Pd, calculated as metal.

The activity of the resulting silicon carbide-supported palladium catalyst for purification of an impure terephthalic acid containing 4-carboxybenzaldehyde (4-CBA) was determined by a batch autoclave reaction test. The impure product was a crude terephthalic acid product comprising terephthalic acid and about 3000 ppmw 4-CBA that had been prepared commercially by liquid phase reaction of p-xylene with oxygen in acetic acid solvent using a bromine-promoted, catalyst containing cobalt and manganese at elevated temperature and pressure.

A 290 g quantity of the crude terephthalic acid product was dissolved in 1160 g deionized water by heating to about 277° C. and stirring at 300 rpm in a 1-gallon, agitated titanium batch autoclave reactor. The reactor had a 20-mesh titanium wire screen basket containing 10 cc of the Pd/SiC catalyst suspended over the liquid phase in the reactor. Weight of catalyst in the screen basket was 8.3 g. Hydrogen was added to the autoclave to a pressure of 50 psia. The agitator stirring rate was increased to 1000 rpm and the screen basket with catalyst was lowered into the liquid phase of the autoclave. Liquid samples were withdrawn at various times after the start of the reaction and analyzed by capillary electrophoresis for 4-CBA, p-toluic acid ("PTOL") and benzoic acid ("BA"). Results are shown in Table 1 below.

TABLE 1

| Time After Start (min.) | 4-CBA (ppmw) | PTOL (ppmw) | BA (ppmw) |
| --- | --- | --- | --- |
| 0 | 3024 | 236 | 435 |
| 10 | 2470 | 897 | 868 |
| 20 | 1393 | 1083 | 847 |
| 30 | 891 | 1390 | 982 |
| 60 | 288 | 1874 | 1094 |
| 120 | 93 | 2975 | 1641 |

For comparison, the procedure described above was repeated using the silicon carbide without added palladium. Results are reported in Table 2.

TABLE 2

| Time After Start (min.) | 4-CBA (ppmw) | PTOL (ppmw) | BA (ppmw) |
| --- | --- | --- | --- |
| 0 | 3107 | 302 | 644 |
| 10 | 3271 | 293 | 560 |
| 20 | 3704 | 320 | 665 |
| 30 | 3943 | 364 | 804 |
| 60 | 3356 | 320 | 753 |
| 120 | 3626 | 431 | 1194 |

Example 1 and TABLES 1 and 2 indicate that the process using the high surface area silicon carbide-supported catalyst was very effective in reducing the concentration of 4-CBA in the terephthalic acid solution. Concomitant production of p-toluic acid, which is a product of 4-CBA hydrogenation that is more easily removed from terephthalic acid by crystallization, was observed in the process. The silicon carbide without palladium displayed essentially no activity for 4-CBA conversion or production of p-toluic acid.

EXAMPLE 2

A sample of catalyst containing 0.9 wt % palladium supported on the silicon carbide as used in Example 1 and made by the incipient wetness impregnation and hydrogen reduction steps substantially as in Example 1 was analyzed for surface area by the BET method. Surface area was 20 m$^2$/g.

EXAMPLE 3

To evaluate physical degradation of the silicon carbide-supported catalysts, such as by abrasion or pressure, a 100-g sample of the silicon carbide material used in Example 1 was tested for attrition and abrasion according to the procedure of ASTM D 4058. The sample was rotated for thirty minutes at 60 rotations per minute, corresponding to 1800 total rotations, in a cylindrical metal drum with an internal baffle. After being rotated in the drum, the silicon carbide material was removed and passed through a No. 20 ASTM sieve with opening size corresponding to 850 µm. For comparison, a sample of a conventional commercial catalyst for purification of terephthalic acid containing 0.5 wt % palladium supported on 4-8 mesh granular carbon was tested in the same manner.

Weight of the silicon carbide sample passing through the test sieve was 0.76 g, corresponding to a 0.76 wt % loss in the ASTM test. In contrast, an average of two tests of the carbon-supported catalyst showed 1.4-1.5 g passing through the test sieve, representing a 1.4-1.5 wt % loss, or essentially double that of the silicon carbide.

EXAMPLE 4

In this example, stability of the high surface area silicon carbide supports in water and in an aqueous terephthalic acid solution at purification process temperatures and pressures were studied.

A 100.9 gram sample of silicon carbide in the form of 3 mm diameter extruded pellets and having a BET surface area of 21 m$^2$/gram and attrition loss of less than 1% according to ASTM D 4058 was placed in a wire screen basket, which was then placed in a 1-gallon titanium batch autoclave autoclave reactor equipped with an internal impeller. The reactor was charged with 2 liters of deionized water, after which it was pressurized to about 950 psig, heated to about 280° C. and agitated by rotation of the impeller at a rate of 300 rpm. The reactor was maintained under those conditions for about one hour and then depressured to drain the water. Charging the reactor with a fresh 2-liter volume of water, pressurizing, heating and agitating the reactor were repeated two more times. After completing the third exposure, the autoclave was allowed to cool and the pellets were removed, dried in a vacuum oven and weighed.

The dried pellets weighed 96.9 grams, indicating a weight loss of 3.9 wt %. The weight loss may have been attributable to silica present on the surface of the initial silicon carbide sample.

The silicon carbide pellets used in the water stability trial described above were loaded into a screen basket and then placed inside an autoclave as in the water stability trial. 2.22 kg of an aqueous, 20 wt % terephthalic acid solution were added to the autoclave and the autoclave was heated to 277° C. and pressurized with hydrogen to about 850 psig. The sample was held at those conditions for 21 days. Samples of the solution were taken periodically, filtered to separate solids and the resulting solids and filtrate were analyzed for silicon content. After 21 days the sample was removed from the autoclave, washed to remove terephthalic acid, dried, and reweighed. The sample weighed 95.8 grams, corresponding to a weight loss of about 1.1 wt %.

Silicon contents of solids and filtrate removed during the test were as follows:

| Time of Sampling (after start of test) | Si Content (ppmw) in | |
|---|---|---|
| | Filtered Solid | Filtrate |
| 0 | 115 | 41 |
| 1 hour | 345 | 190 |
| 1 day | 335 | 500 |
| 2 days | 260 | 540 |
| 3 days | 340 | 525 |
| 7 days | 250 | 590 |
| 9 days | 270 | 620 |
| 14 days | 190 | 630 |
| 17 days | 190 | 660 |

EXAMPLE 5

Separate compartments of a compartmented, titanium wire screen basket were charged with weighed amounts of silicon carbide samples designated 5A and 5B, both obtained from SICAT Corporation in the form of 3-mm diameter extrudates. Sample weights charged to the compartments of the basket were 189.1 g of Sample 5A and 233.5 g of Sample 5B. X-ray diffraction analysis of Sample 5A indicated that it was predominantly silicon carbide in beta crystalline form.

The screen basket charged with the weighed amounts of Samples 5A and 5B was placed within a bed of conventional carbon-supported palladium catalyst in a commercial-scale reactor used for purification of impure terephthalic acid and allowed to remain in the bed during a test period of 133 days during which the reactor was operated substantially continuously for manufacture of purified terephthalic acid from a solution in water of about 25-30 wt % impure terephthalic acid made by liquid phase oxidation of para-xylene. Typical reactor operating conditions during the test period included temperature of about 275-285° C., reactor pressure of about 1000-1200 psig, liquid feed rate of about 550-700 gallons per minute and a gaseous hydrogen flow rate of about 50-90 standard ft.$^3$/minute ("scfm"). At the end of the test period, the reactor was flushed with deionized water, cooled, washed with dilute sodium hydroxide solution for 2.5 hours, and then washed with deionized water. The screen basket was removed from the reactor and dried in a vacuum oven at 70° C. The samples were removed from the basket for inspection and analysis.

Visual inspection of the samples removed from the screen basket after testing showed no obvious damage. Extrudate diameters of both samples were measured and found to be within 2% of their initial 3-mm diameters.

Samples 5A and 5B removed from the screen basket were weighed. Sample 5A weighed 163.3 g, indicating a 13.6% weight loss from the initial charge of the sample and Sample 5B weighed 203.6 g, indicating a 12.8% weight loss from the sample as charged. Some of the weight losses of these samples may be attributable to dissolution and removal of silica impurities under conditions to which the samples were exposed during the test period.

X-ray diffraction analysis of sample 5A after testing showed that the sample was predominantly beta crystallites of silicon carbide. For Sample 5A removed from the screen basket after the test period, bulk density was also determined and the sample was tested as in Example 3 for attrition loss, for BET surface area and for pore volume by mercury porosimetry. Results of those tests, and results of the same tests of Sample 5A before charging to the screen basket, are reported in TABLE 3 below.

TABLE 3

|  | Before Testing | After Testing |
|---|---|---|
| Bulk Density (g/cm³) | 0.71 | 0.63 |
| Attrition Loss (%) | 0.9 | 2.0 |
| BET Surface Area (g/m²) | 27.5 | 35.0 |
| Pore Volume (cm³/g) | 0.52 | 0.66 |

Attrition losses of about 1.5 to about 3.0 wt % after at least 100 days substantially continuous use with flows of hydrogen and 25 wt % or greater aqueous aromatic carboxylic acid solution at temperature of about 275° C. or above and pressure of at least about 1000 psig are indicative of substantial stability under process conditions. Attrition loss of Sample 5A after testing, though more than the initial attrition loss of the untested sample, is comparable to that of catalysts supported oh conventional granular carbon supports commonly used for purification of terephthalic acid.

EXAMPLE 6

A small quantity of silicon carbide Sample 5A, as described in Example 5, was provided to a commercial catalyst manufacturer for use as a support for preparing an experimental catalyst composition with 0.5 wt % palladium. Activity of the resulting catalyst received from the catalyst manufacturer was tested by purifying impure terephthalic acid containing 4-CBA substantially as in Example 1. Results are reported in TABLE 4.

TABLE 4

| Time After Start (min.) | 4-CBA (ppmw) | PTOL (ppmw) | BA (ppmw) |
|---|---|---|---|
| 0 | 3079 | 254 | 385 |
| 10 | 1751 | 537 | 753 |
| 20 | 974 | 879 | 1030 |
| 30 | 463 | 1174 | 1187 |
| 60 | 135 | 1502 | 1356 |

Comparing TABLES 1 and 4, it is evident that the decrease in 4-CBA concentration with time was faster in this example than in Example 1, indicating a more active catalyst in this example than in Example 1.

We claim:

1. A process for purifying an aromatic carboxylic acid comprising contacting with hydrogen under hydrogenation conditions at a temperature of about 200 to about 370° C. and in the presence of a catalyst an aqueous solution comprising an aromatic carboxylic acid, wherein the catalyst comprises particulates comprising a Group VIII hydrogenation catalyst metal disposed substantially on the surface of a support comprising silicon carbide having a BET surface area of at least about 10 m²/g and the catalyst has an initial attrition loss according to ASTM D-4058 up to about 1.2 wt % and the silicon carbide is stable in the aqueous solution under the hydrogenation reaction conditions such that stability of the catalyst is indicated by weight loss of less than about 2 wt % after 20 days exposure to an aqueous 20 wt % solution of terephthalic acid solution at about 275° C. and 850 psig.

2. The process of claim 1 wherein the catalyst contains about 0.1 to about 5 wt % hydrogenation catalyst metal.

3. The process of claim 2 wherein the hydrogenation catalyst metal comprises palladium.

4. The process of claim 1 wherein the aromatic carboxylic acid comprises terephthalic acid.

5. The process of claim 1 wherein the aromatic carboxylic acid comprises a crude aromatic carboxylic acid product obtained by liquid phase oxidation of a feed material comprising an aromatic compound with one or more substituents oxidizable to a carboxylic acid group and comprises aromatic carboxylic acid and at least one oxidation intermediate or by-product.

6. The process of claim 5 wherein the crude aromatic carboxylic acid product comprises terephthalic acid.

7. The process of claim 1 wherein the aromatic carboxylic acid comprises aromatic carboxylic acid and at least one aromatic carbonyl compound that forms a hydrogenated compound more soluble in aqueous solution than the aromatic carbonyl compound and than the aromatic carboxylic acid or with less color or color-forming tendencies.

8. The process of claim 7 wherein the aromatic carbonyl compound comprises at least one of benzaldehyde, 2-, 3- and 4-carboxybenzaldehyde, 2,6-dicarboxyfluorenone and 2,6-dicarboxyanthroquinone.

9. The process of claim 1 further comprising separating from the hydrogenated aqueous reaction liquid a solid aromatic carboxylic acid product.

10. A process for manufacture of a purified aromatic carboxylic acid product comprising steps comprising contacting a feed material comprising an aromatic compound with oxidizable substituents with oxygen in the presence of a heavy metal catalyst in a liquid reaction mixture under oxidation reaction conditions;

separating from the liquid reaction mixture a crude product comprising aromatic carboxylic acid and at least one oxidation intermediate or by-product;

forming an aqueous solution comprising the crude product;

contacting the aqueous solution with hydrogen in the presence of a catalyst in particulate form under hydrogenation reaction conditions at a temperature of about 200 to about 370° C., wherein the catalyst particles comprise a Group VIII hydrogenation catalyst metal disposed substantially on the surface of a support comprising silicon carbide having a BET surface area of at least about 10 m²/g, the catalyst has an initial attrition loss according to ASTM D-4058 up to about 1.2 wt % and the silicon carbide is stable in the aqueous solution under the hydrogenation reaction conditions such that stability of the catalyst is indicated by weight loss of less than about 2 wt % after 20 days exposure to an aqueous 20 wt % solution of terephthalic acid solution at about 275° C. and 850 psig.

11. The process of claim 10 wherein the oxidation intermediate or by-product comprises at least one carboxybenzaldehyde.

12. The process of claim 10 wherein the oxidation intermediate or by-product comprises 4-carboxybenzaldehyde.

13. The process of claim 12 wherein the catalyst metal comprises palladium.

14. The process of claim 10 wherein the catalyst has a BET surface area of at least about 20 m² μg.

15. A process for purification of an aromatic carboxylic acid product comprising terephthalic acid and at least one impurity comprising 4-carboxybenzaldehyde, hydroxymethyl benzoic acid, p-toluic acid, 2,6-dicarboxyfluorenone, 2,6-dicarboxyanthroquinone, 2,4',5-tricarboxybiphenyl, 2,5-dicarboxyphenyl-4-carboxyphenyl methane, 3,4'- and 4,4'-dicarboxybiphenyl, and 2,6-dicarboxyfluorene comprising contacting an aqueous solution of the product with hydrogen in the presence of a catalyst in particulate form under hydrogenation reaction conditions at a temperature of about 200 to about 370° C., wherein the catalyst particles comprises a Group VIII hydrogenation catalyst metal disposed substantially on the surface of a support comprising silicon carbide having a BET surface area of at least about 10 $m^2/g$, the catalyst has an initial attrition loss according to ASTM D-4058 up to about 1.2 wt % and the silicon carbide is stable in the aqueous solution under the hydrogenation reaction conditions such that stability of the catalyst is indicated by weight loss of less than about 2 wt % after 20 days exposure to an aqueous 20 wt % solution of terephthalic acid solution at about 275° C. and 850 psig; and recovering from the hydrogenated aqueous solution a purified terephthalic acid.

16. A process for manufacture of terephthalic acid in purified form comprising steps comprising contacting under oxidation reaction conditions a feed material comprising p-xylene with oxygen in the presence of a heavy metal catalyst in a liquid reaction mixture that includes a solvent comprising a low molecular weight monocarboxylic acid and water;

separating from the liquid reaction mixture a crude product comprising terephthalic acid and at least one oxidation intermediate or by-product;

forming an aqueous solution comprising about 5 to about 50 parts by weight of the crude product per hundred parts by weight solution at process temperature;

contacting the aqueous solution with hydrogen in the presence of a catalyst in particulate form at a temperature of about 200 to about 370° C. under pressure effective to maintain a liquid phase comprising the reaction solution, wherein the catalyst particles comprise a Group VIII hydrogenation catalyst metal disposed substantially on the surface of a support comprising silicon carbide having a BET surface area of at least about 10 $m^2/g$, the catalyst has an initial attrition loss according to ASTM D-4058 up to about 1.2 wt % and the silicon carbide is stable in the aqueous solution under the hydrogenation reaction conditions such that stability of the catalyst is indicated by weight loss of less than about 2 wt % after 20 days exposure to an aqueous 20 wt % solution of terephthalic acid solution at about 275° C. and 850 psig; and recovering from the hydrogenated aqueous solution a purified terephthalic acid with a reduced oxidation intermediate or by-product content.

\* \* \* \* \*